(12) United States Patent
Sun et al.

(10) Patent No.: US 12,266,208 B2
(45) Date of Patent: Apr. 1, 2025

(54) BIOMETRIC INFORMATION RECOGNITION MODULE AND ELECTRONIC DEVICE

(71) Applicant: TIANJIN JIIOV TECHNOLOGY CO., LTD., Tianjin (CN)

(72) Inventors: Jiancheng Sun, Beijing (CN); Haisheng Wang, Beijing (CN); Ying Bi, Beijing (CN)

(73) Assignee: TIANJIN JIIOV TECHNOLOGY CO., LTD., Tianjin (CN)

( * ) Notice: Subject to any disclaimer, the term of this patent is extended or adjusted under 35 U.S.C. 154(b) by 0 days.

(21) Appl. No.: 18/569,397

(22) PCT Filed: Jul. 7, 2022

(86) PCT No.: PCT/CN2022/104357
§ 371 (c)(1),
(2) Date: Dec. 12, 2023

(87) PCT Pub. No.: WO2023/280269
PCT Pub. Date: Jan. 12, 2023

(65) Prior Publication Data
US 2024/0273937 A1 Aug. 15, 2024

(30) Foreign Application Priority Data

Jul. 7, 2021 (CN) .......................... 202110768263.7
Jul. 7, 2021 (CN) .......................... 202121542761.1
(Continued)

(51) Int. Cl.
*G06V 40/13* (2022.01)
*G06V 40/12* (2022.01)
(52) U.S. Cl.
CPC ...... *G06V 40/1318* (2022.01); *G06V 40/1324* (2022.01); *G06V 40/1365* (2022.01)

(58) Field of Classification Search
CPC ........... G06V 40/1318; G06V 40/1365; G06V 40/1324; G06V 40/18; G06V 40/12; G06V 40/13; A61B 5/1172
See application file for complete search history.

(56) References Cited

U.S. PATENT DOCUMENTS

2015/0369661 A1* 12/2015 Lin .................... G06V 40/1318
250/227.11
2016/0254312 A1* 9/2016 Lee ................... H01L 27/14687
382/125
(Continued)

FOREIGN PATENT DOCUMENTS

| CN | 109496313 C | 3/2019 |
| CN | 110163159 A | 8/2019 |

(Continued)

OTHER PUBLICATIONS

English translation of the International Search Report and Written Opinion in Application No. PCT/CN2022/104357, mailed Sep. 30, 2022, 15 pages.

(Continued)

*Primary Examiner* — Stephen G Sherman
(74) *Attorney, Agent, or Firm* — Meunier Carlin & Curfman LLC

(57) ABSTRACT

Provided are a biometric information recognition module and an electronic device. The biometric information recognition module includes an optical path guide layer and an optical sensor; the optical path guide layer includes a plurality of optical channels, and the optical sensor includes a plurality of photosensitive pixel units, at least two adjacent photosensitive pixel units forming a photosensitive pixel unit group; the biometric information recognition module further includes a gap region disposed between at least two photosensitive pixel unit groups, and light beams carrying biometric information above the gap region are received by (Continued)

at least one photosensitive pixel unit through the optical channels. The electronic device includes a display screen and a biometric information recognition module disposed under the display screen.

18 Claims, 9 Drawing Sheets

(30) Foreign Application Priority Data

Aug. 23, 2021 (CN) .......................... 202110970555.9
Aug. 23, 2021 (CN) .......................... 202121992729.3

(56) References Cited

U.S. PATENT DOCUMENTS

| | | | |
|---|---|---|---|
| 2018/0268190 A1* | 9/2018 | Chung | G06F 3/041 |
| 2018/0286925 A1 | 10/2018 | Kim et al. | |
| 2021/0028406 A1* | 1/2021 | Sun | H10K 59/8791 |
| 2021/0042494 A1* | 2/2021 | Xie | G06V 40/1318 |
| 2025/0005958 A1* | 1/2025 | Sun | G06V 10/751 |

FOREIGN PATENT DOCUMENTS

| | | |
|---|---|---|
| CN | 209765529 U | 12/2019 |
| CN | 111095282 A | 5/2020 |
| CN | 111108511 A | 5/2020 |
| CN | 111353405 A | 6/2020 |
| CN | 211180842 U | 8/2020 |
| CN | 111801679 A | 10/2020 |
| CN | 112860120 A | 5/2021 |
| CN | 113780103 A | 12/2021 |
| CN | 216161104 U | 4/2022 |
| EP | 3800579 A1 | 4/2021 |
| WO | 2021082680 A1 | 5/2021 |

OTHER PUBLICATIONS

English translation of the First Office Action in Chinese Application No. 202110970555.9 dated Jun. 30, 2023, 22 pages.

* cited by examiner

BIOMETRIC INFORMATION RECOGNITION MODULE AND ELECTRONIC DEVICE

CROSS REFERENCES

This is a U.S. national stage application of international patent application number PCT/CN2022/104357 filed on Jul. 7, 2022, and claiming priority to the Chinese patent application No. 202110970555.9 filed on Aug. 23, 2021; the Chinese patent application No. 202121992729.3 filed on Aug. 23, 2021; the Chinese patent application No. 202110768263.7 filed on Jul. 7, 2021; and the Chinese patent application No. 202121542761.1 filed on Jul. 7, 2021.

TECHNICAL FIELD

The present disclosure relates to the technical field of electronic devices and specifically relates to a biometric information recognition module (bio-information recognition module) and an electronic device.

BACKGROUND ART

With the rapid development of smart terminal electronic devices, primarily led by handheld mobile terminals, the application of human bio-information recognition in electronic devices has become increasingly extensive and profound. It has evolved from the previous use of bio-information recognition for unlocking and waking up electronic devices to various software programs for identity recognition and authentication. With the widespread application of bio-information recognition in electronic devices, the accuracy of bio-information recognition and the recognition capability and speed of electronic devices, especially display-based electronic devices, for fingerprint information, have been improved accordingly.

In the related technology, bio-information recognition applied to electronic devices such as smartphones and tablets, for example, fingerprint recognition, primarily utilizes optical fingerprint recognition. Typically, this method involves illuminating fingerprints with a light source from the display panel and reflecting the light, and then capturing, recording, or analyzing the reflected light carrying specific bio-information using optical detection devices to achieve the function of recording fingerprints or identifying specific fingerprints. In recent years, with the increasing demand for miniaturization of electronic devices such as smartphones and tablets, there has been a growing need for the thinning and downsizing of fingerprint recognition modules placed inside these electronic devices. This, in turn, necessitates a continuous reduction in the volume of the optical detection devices used to achieve fingerprint recognition. To ensure the accuracy of bio-information recognition, the collection area for bio-information on the display screen should be at least maintained within a relatively small area range. This results in challenges in further reducing the size of fingerprint recognition modules, significantly impacting the miniaturization of electronic devices.

SUMMARY

The embodiments of the present disclosure provide a bio-information recognition module and an electronic device, capable of receiving a larger area range of light beams carrying bio-information without increasing the overall volume of the module.

The embodiments of the present disclosure provide a bio-information recognition module, wherein the bio-information recognition module can comprise an optical path guiding layer and an optical sensor. The optical path guiding layer comprises multiple optical channels, and the optical sensor comprises multiple photosensitive pixel units, with adjacent at least two photosensitive pixel units forming a photosensitive pixel unit group. The bio-information recognition module further comprises a gap region provided between at least two photosensitive pixel unit groups. Light beams carrying bio-information above the gap region are received by at least one photosensitive pixel unit through the optical channels.

Optionally, the optical channels can comprise inclined optical channels, wherein the inclined optical channels form an angle with the straight line that is perpendicular to a surface of the optical sensor.

Optionally, the photosensitive pixel units can comprise a first photosensitive pixel unit, wherein the first photosensitive pixel unit receives light beams above the gap region adjacent to the first photosensitive pixel unit through the inclined optical channel.

Optionally, the inclined optical channel corresponding to the first photosensitive pixel unit can be tilted toward the center of the photosensitive pixel unit group along the direction of the light beams.

Optionally, the photosensitive pixel units can comprise a first photosensitive pixel unit, wherein the first photosensitive pixel unit receives light beams above the gap region adjacent to other photosensitive pixel units, excluding the first photosensitive pixel unit, through the inclined optical channel.

Optionally, the other photosensitive pixel units, excluding the first photosensitive pixel unit, can comprise a photosensitive pixel unit positioned on the opposite side of the first photosensitive pixel unit within the same photosensitive pixel unit group.

Optionally, within the photosensitive pixel unit group, the inclined optical channels corresponding to two photosensitive pixel units that are symmetric with respect to the center of the photosensitive pixel unit group can intersect above the center.

Optionally, in multiple inclined optical channels corresponding to one photosensitive pixel unit group, angles of two inclined optical channels that are symmetric with respect to the center of the photosensitive pixel unit group can be the same.

Optionally, in multiple inclined optical channels corresponding to one photosensitive pixel unit group, angles of the inclined optical channels that correspond to the photosensitive pixel units equidistant from the center of the photosensitive pixel unit group can be the same.

Optionally, in multiple inclined optical channels corresponding to one photosensitive pixel unit group, an angle of the inclined optical channels that are closer to the center of the photosensitive pixel unit group can be smaller than or equal to an angle of the inclined optical channels that are farther from the center of the photosensitive pixel unit group.

Optionally, the optical path guiding layer can comprise at least two layers of light-shielding layers that are provided at intervals. On the light-shielding layers, diaphragm openings can be formed, and at least two diaphragm openings corresponding to the at least two layers of the light-shielding layers form at least a portion of the optical channels.

Optionally, the optical path guiding layer can comprise a micro lens group arranged on the light-shielding layers. The micro lens group comprises multiple micro lens units, and the micro lens units form at least a portion of the optical channels.

Optionally, the light beams carrying bio-information can be received by one photosensitive pixel unit group through one micro lens unit.

Optionally, the multiple photosensitive pixel units forming the photosensitive pixel unit group can be combined in an N*M pattern, wherein N is an integer greater than or equal to 1, and M is an integer greater than or equal to 2.

Optionally, the gap region can be formed on the optical sensor as at least one strip-shaped region or at least one horizontal-and-vertical cross-connect region.

Optionally, the gap region can comprise a first reserved region configured for laying out circuit signal lines.

Optionally, the gap region can also comprise a second reserved region configured for arranging circuit components.

In another aspect of the embodiments of the present disclosure, an electronic device is provided, wherein the electronic device can comprise a display screen and a bio-information recognition module provided under the display screen, as described in any of the previous sections.

Optionally, a bio-information recognition region can be arranged on the display screen. The bio-information recognition region comprises multiple sections corresponding to multiple photosensitive pixel unit groups. Light beams carrying biological feature information from the sections are received by the corresponding photosensitive pixel unit groups through the optical channels.

Optionally, an area of orthographic projection of at least one section on the optical sensor can be greater than the area of its corresponding photosensitive pixel unit group.

Optionally, the orthographic projections of at least two adjacent sections can have an overlapping region on the optical sensor.

Optionally, the overlapping region can be rectangular, and a width of the overlapping region can be between 3-5 micrometers.

Beneficial effects of the present disclosure can comprise at least the following.

The present disclosure provides a bio-information recognition module comprising an optical path guiding layer and an optical sensor. The optical path guiding layer comprises multiple optical channels, and the optical sensors comprise multiple photosensitive pixel units, with adjacent at least two photosensitive pixel units forming a photosensitive pixel unit group. The bio-information recognition module further comprises a gap region provided between at least two photosensitive pixel unit groups. Light beams carrying bio-information above the gap region are received by at least one photosensitive pixel unit through the optical channels. This way, in usage, light beams carrying bio-information can be transmitted through multiple optical channels to the optical sensor, where they are received and recognized by the photosensitive pixel units of the optical sensor. Simultaneously, light beams carrying bio-information above the gap region can also be received by at least one photosensitive pixel unit through the optical channels, and their normal transmission remains unaffected. In the present disclosure, the gap region is arranged between at least two photosensitive pixel unit groups and it is ensured that light beams carrying bio-information above the gap region are received by at least one photosensitive pixel unit through the optical channels. In this way, on one hand, the present disclosure allows a larger area range of light beams carrying bio-information to enter the optical sensor, which effectively increases the collection area for bio-information of the display screen without changing the total area of the photosensitive pixel unit (i.e., the area of the photosensitive region). This, in turn, enables the bio-information recognition module to receive more optical signals of light beams carrying bio-information. In turn, more bio-information is obtained, thus contributing to the accuracy of bio-information recognition. On the other hand, without the need to increase the bio-information collection area of the display screen, the present disclosure can improve the effective utilization rate of the total area of photosensitive pixel units (i.e., the area of the photosensitive region) in the optical sensor. This reduces the area of the photosensitive region of the optical sensor, thus reducing the size of the optical sensor. This, in turn, saves more internal space for electronic devices using the bio-information recognition module provided by the present disclosure while lowering the cost of the bio-information recognition module.

BRIEF DESCRIPTION OF DRAWINGS

In order to more clearly illustrate the technical solutions of the embodiments of the present disclosure, the following will briefly introduce the drawings used in the embodiments. It should be understood that the following drawings only show some embodiments of the present disclosure, and therefore it should not be regarded as a limitation on the scope. Those ordinary skilled in the art can also obtain other related drawings based on these drawings without inventive effort.

Figure 1:
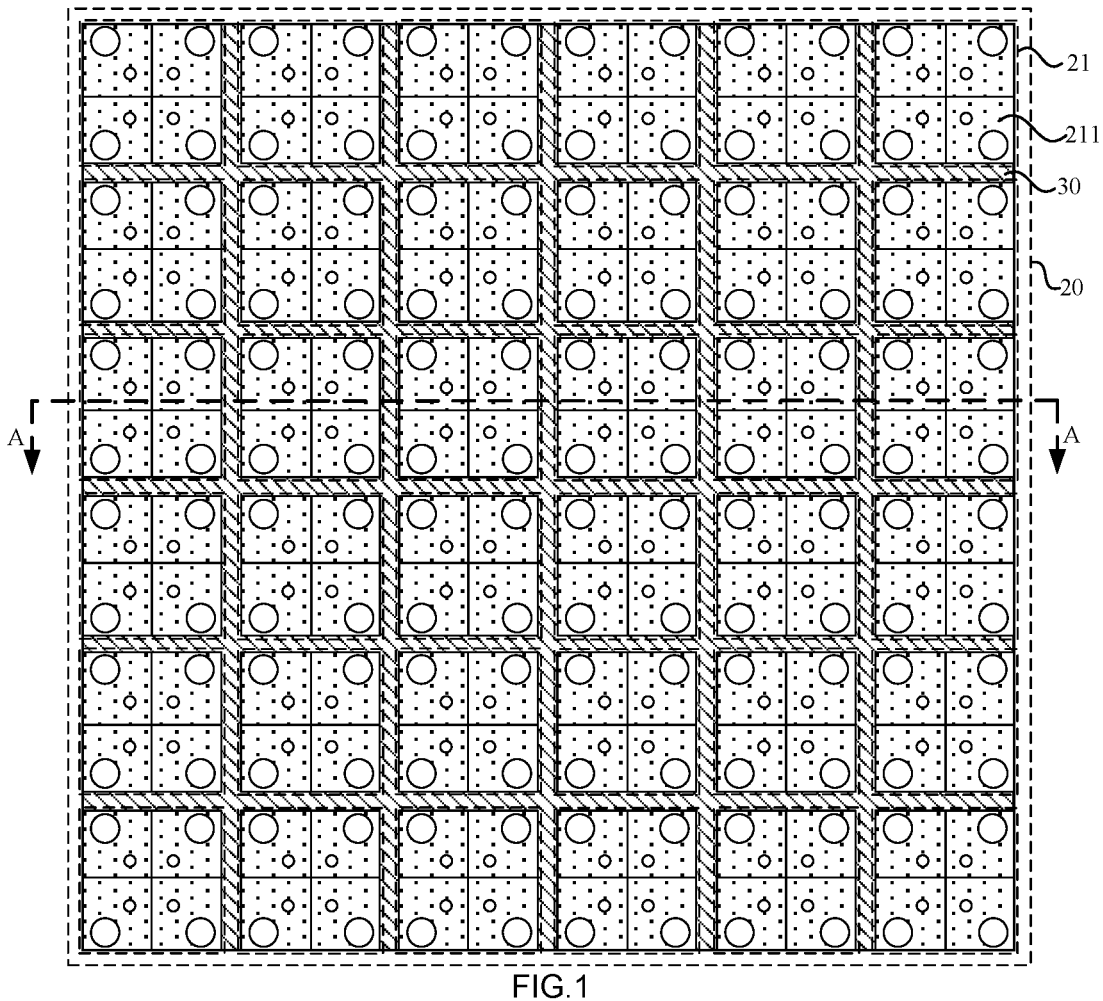
FIG. 1 is the first schematic structural diagram of a bio-information recognition module provided in the embodiments of the present disclosure.

Reference numerals: 10—optical path guiding layer; 11—optical channel; 111—inclined optical channel; θ—angle between the inclined optical channel and the straight line perpendicular to the surface of the optical sensor; 12A—first light-shielding layer; 12B—second light-shielding layer; 121—first diaphragm opening; 122—second diaphragm opening; 13—micro lens group; 131—micro lens unit; 20—optical sensor; 21—photosensitive pixel unit group; 211, 211a, 211b, 211c, 211d, 211e, 211f, 211g, 211h, 211i, 211j, 211n, 211r, 211s, 211t, 211u, 211v—photosensitive pixel unit; 211A—first photosensitive pixel unit; 211B—other photosensitive pixel unit; 30—gap region; 31—first gap region; 32—second gap region; 40—display screen; 41—bio-information recognition region; 411—section; 412—overlapping region; W3—width of the overlapping region.

DETAILED DESCRIPTION OF EMBODIMENTS

The following description will combine the drawings in the embodiments of the present disclosure to provide a clear and comprehensive explanation of the technical solution in the embodiments of the present disclosure.

In the description of the present disclosure, it should be noted that the orientation or position relationships indicated by the terms "inside", "outside", etc. are the orientation or position relationships shown based on the drawings or the orientation or position relationships customarily placed in the use of the product of the present disclosure. It is only for the convenience of describing the present disclosure and simplifying its description and does not indicate or imply that the device or element referred to must be in a specific orientation or be constructed and operated in a specific orientation, and thus should not be construed as limiting the present disclosure. In addition, the terms "first" and "second" are only used to distinguish the descriptive and are not to be construed as indicating or implying relative importance.

In the description of the present disclosure, it should be noted that, unless otherwise clearly stipulated and limited, the terms "provide" and "connect" should be understood in a broad sense, for example, it can be a fixed connection, a detachable connection, or an integral connection, and it can be a direct connection, an indirect connection through an intermediary, or an internal communication between two components. Those of ordinary skill in the art can understand the meanings of the above terms in the present disclosure according to specific situations.

Biometric recognition technology has been widely applied to various terminal devices and electronic apparatuses. Biometric recognition technology includes but is not limited to fingerprint recognition, palm print recognition, vein recognition, iris recognition, facial recognition, live recognition, anti-counterfeiting recognition, and more. Among these, fingerprint recognition typically includes optical fingerprint recognition, capacitive fingerprint recognition, and ultrasonic fingerprint recognition. With the rise of full-screen technology, fingerprint recognition modules can be arranged in a localized region or the entire region under the display, thus forming under-display optical fingerprint recognition. Alternatively, parts or all of the optical fingerprint recognition module can be integrated into the display screen of electronic devices, thus creating in-display optical fingerprint recognition. The display screen can be an organic light emitting diode (OLED) screen or a liquid crystal display (LCD), among others. Fingerprint recognition methods generally involve steps such as fingerprint image acquisition, preprocessing, feature extraction, feature matching, and more. Some or all of these steps can be implemented using traditional computer vision (CV) algorithms or deep learning algorithms based on artificial intelligence (AI). Fingerprint recognition technology can be applied in various portable or mobile terminals such as smartphones, tablets, gaming devices, as well as other electronic devices like smart locks, cars, and ATMs, for fingerprint unlocking, fingerprint payment, fingerprint attendance, identity authentication, and more.

For bio-information recognition modules applied under the display screen, it is typically necessary to confirm and identify the individual to whom specific biological information belongs by receiving, recording, or analyzing the reflected light carrying the specific bio-information. The display screen is placed over the bio-information recognition module, its primary function is to display the required information. Therefore, the collection area divided for under-display bio-information recognition is quite limited. Furthermore, for the extraction of biological information, there is a need for a sufficient amount of light beams carrying bio-information as a foundation to derive accurate recognition data. Based on this, the more light beams with bio-information the module can obtain, the more its recognition accuracy, anti-interference capability, and ability to recognize counterfeit can be correspondingly enhanced. Therefore, how to effectively obtain as many reflected light beams carrying specific bio-information as possible within this limited bio-information collection area and process these reflected light beams to extract as much specific bio-information as possible is a critical challenge that needs to be addressed and improved in the practical application of bio-information recognition modules. This is essential for enhancing the accuracy of confirming and identifying individuals based on their biological feature information.

Of course, bio-information recognition modules do not necessarily have to be integrated under a display screen of a display device. In other feasible application scenarios, bio-information modules can exist as standalone modules specifically configured for bio-information recognition. For example, it is possible to arrange a transparent protective glass panel or protective film layer on the bio-information module, allowing light beams carrying bio-information to pass through the protective glass panel to enter the bio-information recognition module, which in turn is recognized by the bio-information recognition module.

Figure 2:
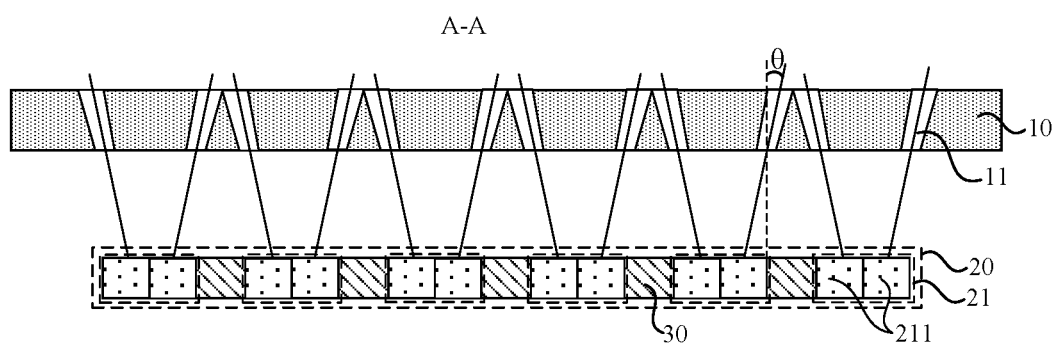
FIG. 2 is a sectional view at A-A in FIG. 1.

Based on this, referring to FIGS. 1 and 2, embodiments of the present disclosure provide a bio-information recognition module. The bio-information recognition module can be a fingerprint recognition module, wherein the bio-information recognition module can comprise an optical path guiding layer 10 and an optical sensor 20. The optical path guiding layer 10 can comprise multiple optical channels 11, and the optical sensors 20 comprise multiple photosensitive pixel units 211, with adjacent at least two photosensitive pixel units 211 forming a photosensitive pixel unit group 21. The bio-information recognition module further comprises a gap region 30 provided between at least two photosensitive pixel unit groups 21. Light beams carrying bio-information above the gap region 30 are received by at least one photosensitive pixel unit 211 through the optical channels 11.

It is important to note that the bio-information recognition module in the embodiment can be applied to common terminal devices such as smartphones, tablets, and other handheld display devices, as well as household LCD appliances like televisions, desktop computers, air conditioners, refrigerators, and more. Additionally, the bio-information recognition module is configured to identify light beams carrying biological information, for example, the light beams carrying bio-information can originate from palm prints of human palms, palm veins, joint patterns, irises, faces, and more. As an example, but not as a limitation, the biological information can be fingerprints from human fingers. To facilitate understanding, the following description will mainly use fingerprint recognition on handheld display devices, which is commonly encountered in real life, as an example.

FIG. 2 provides a structural schematic diagram of a bio-information recognition module according to the embodiment of the present disclosure. As shown in FIG. 2, the bio-information recognition module can comprise an optical path guiding layer 10 and an optical sensor 20 provided in the top and bottom orientations as illustrated in FIG. 2. The optical path guiding layer 10 can be located above the optical sensor 20, and the optical path guiding layer 10 can comprise multiple optical channels 11. The multiple optical channels 11 can be configured to allow light beams carrying bio-information to pass through, thereby being incident in the optical sensor 20. It should be noted that, in the embodiment, the aforementioned multiple optical channels 11 can be arranged in a matrix form on the optical path guiding layer 10 or they can be arranged in an annular shape on the optical path guiding layer 10; and the present disclosure does not impose a specific constraint on this. Additionally, the sectional shape of the optical channel 11 can be a slanted square (parallelogram) or a slanted trapezoid that is larger on top and smaller at the bottom, among others, as long as it allows as many light beams carrying bio-information as possible to pass through the optical channel 11 and be efficiently received by the optical sensor 20. For instance, when the sectional shape of the optical channel 11 is a slanted trapezoid, in order to reduce the loss of the light beams within the optical channel 11, a reflective film can be correspondingly arranged inside the optical channel 11. Specifically, when the sectional shape of the optical channel 11 is a slanted trapezoid, the corresponding optical components arranged inside the optical channel 11 can be specifically arranged and set up by those skilled in the art based on actual conditions.

Figure 3:
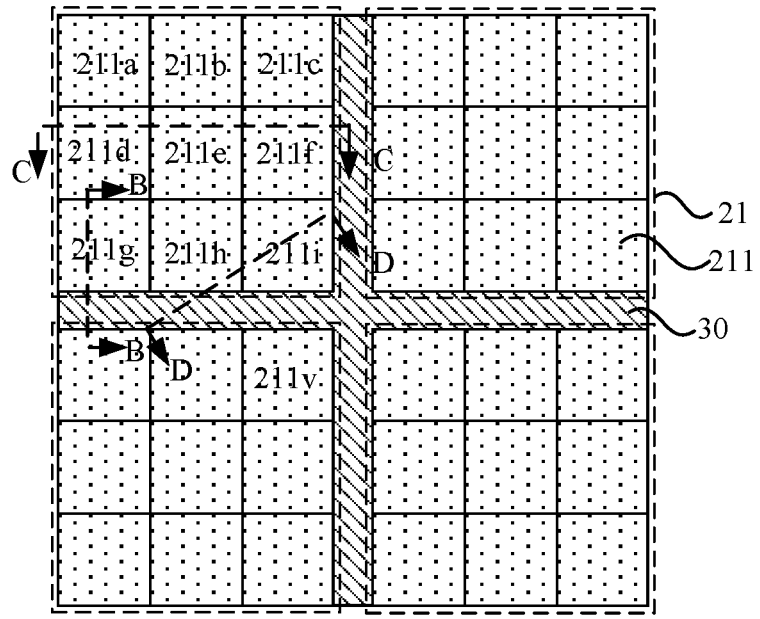
FIG. 3 is the first schematic structural diagram of an optical sensor in the bio-information recognition module provided by the embodiments of the present disclosure.

As shown in FIG. 3, the aforementioned optical sensor 20 can comprise multiple photosensitive pixel units 211, with adjacent photosensitive pixel units 211 forming a photosensitive pixel unit group 21. In this case, each photosensitive pixel unit 211 of the optical sensor 20 can receive incident light beams carrying bio-information. The number and location of photosensitive pixel units 211 that make up the photosensitive pixel unit group 21 are not specifically defined in the embodiments of the present disclosure. Multiple photosensitive pixel units 211 within the same photosensitive pixel unit group 21 should be adjacent to each other. For example, at least two adjacent photosensitive pixel units 211 can form a photosensitive pixel unit group 21. Alternatively, three sequentially adjacent photosensitive pixel units 211 can form a rectangular-shaped photosensitive pixel unit group 21. It is also possible, for example, that the multiple photosensitive pixel units 21 forming the photosensitive pixel unit group 211 are combined in an N*M pattern, wherein N is an integer greater than or equal to 1, and M is an integer greater than or equal to 2. For instance, the multiple photosensitive pixel units 211 forming the photosensitive pixel unit group 21 can be in patterns like 2*2, 2*3, 3*3, 4*4, 4*3, or 5*5, etc., which will not be enumerated in the present disclosure. In the embodiment, N and M can be equal or different. When N and M are equal, it means that multiple photosensitive pixel units 211 forming the photosensitive pixel unit group 21 are combined in an N*N pattern. However, it should be noted that when multiple photosensitive pixel units 211 forming the photosensitive pixel unit group 21 are combined in an N*M pattern, since M is an integer greater than or equal to 2, the present disclosure does not include the pattern of 1*1 for multiple photosensitive pixel units forming the photosensitive pixel unit group 21. That is to say, as long as it is not in the form of one photosensitive pixel unit 211 forming a photosensitive pixel unit group 21, it falls within the combinable patterns of the photosensitive pixel unit group 21 provided in the embodiments of the present disclosure, and it is not enumerated here.

Figure 4:
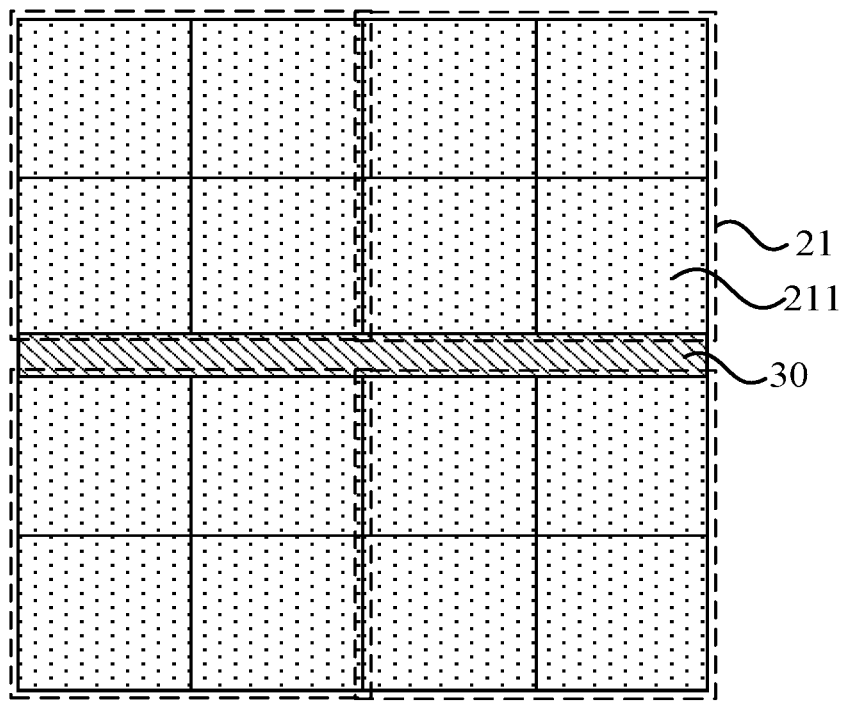
FIG. 4 is the second schematic structural diagram of the optical sensor in the bio-information recognition module provided by the embodiments of the present disclosure.
Figure 5:
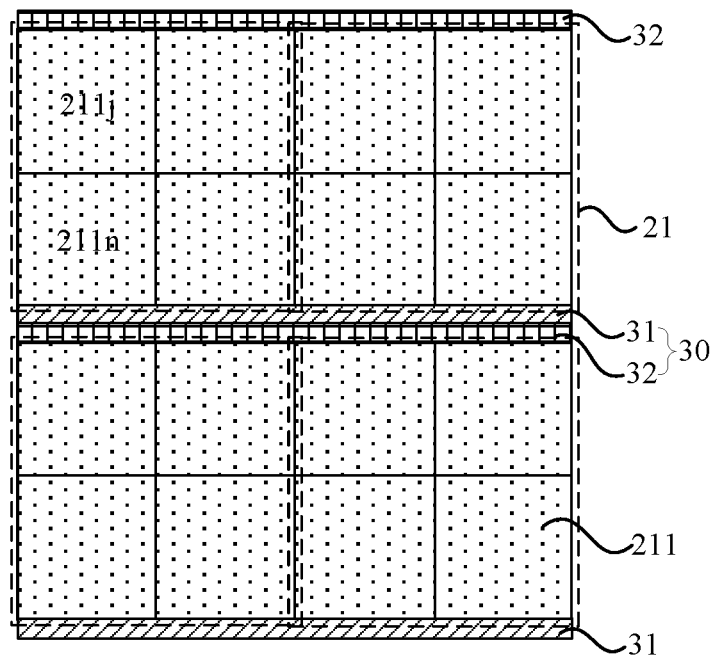
FIG. 5 is the third schematic structural diagram of the optical sensor in the bio-information recognition module provided by the embodiments of the present disclosure.

As shown in FIG. 3, FIG. 3 illustrates multiple photosensitive pixel units 211 comprising a photosensitive pixel unit group 21 presented in a 3*3 pattern, wherein the photosensitive pixel unit group 21 comprises 4 groups. It is important to note that when multiple photosensitive pixel units 211 forming the photosensitive pixel unit group 21 are presented in a 3*3 pattern, the optical sensor 20 is not limited to comprise 4 groups of photosensitive pixel unit groups 21; and it can be more than 4 groups. FIG. 3 is just one example provided by the present disclosure. As shown in FIG. 4, FIG. 4 illustrates multiple photosensitive pixel units 211 comprising a photosensitive pixel unit group 21 presented in a 2*2 pattern, wherein the photosensitive pixel unit group 21 comprises 4 groups. Similarly, when multiple photosensitive pixel units 211 forming the photosensitive pixel unit group 21 are presented in a 2*2 pattern, the optical sensor 20 is not limited to comprise 4 groups of photosensitive pixel unit groups 21; and it can be more than 4 groups. As shown in FIG. 5, FIG. 5 illustrates multiple photosensitive pixel units 211 comprising a photosensitive pixel unit group 21 presented in a 2*4 pattern, wherein the photosensitive pixel unit group 21 comprises 2 groups. Similarly, when multiple photosensitive pixel units 211 forming the photosensitive pixel unit group 21 are presented in a 2*4 pattern, the optical sensor 20 is not limited to comprise 2 groups of photosensitive pixel unit groups 21; and it can be more than 2 groups.

It should be noted that the light-receiving surface of the optical sensor 20 can be flat, or it can be designed as a protruding curved surface, a recessed curved surface, a sloping surface, etc., according to actual needs. In the embodiment, the commonly used form is adopted, that is, the light-receiving surface of the optical sensor 20 is designed as a flat surface. Therefore, the receiving surface of each photosensitive pixel unit group 21 that forms the light-receiving surface of the optical sensor 20 is also flat. The receiving sides of multiple photosensitive pixel units 211 forming a photosensitive pixel unit group 21 collectively form a flat receiving surface of the photosensitive pixel unit group 21. The light-receiving surfaces of multiple photosensitive pixel unit groups 21 together serve as the photosensitive region of the optical sensor 20.

Referring to FIG. 3 to FIG. 5, the bio-information recognition module provided in the embodiment can also comprise a gap region 30 arranged between at least two photosensitive pixel unit groups 21. For instance, the aforementioned gap region 30 can be arranged between every two adjacent photosensitive pixel unit groups 21 (as shown in FIG. 1 and FIG. 3); or it can be arranged between some of the adjacent photosensitive pixel unit groups 21. For example, it can be arranged only between photosensitive pixel unit groups 21 that are distributed vertically, as shown in FIG. 4 and FIG. 5; or it can be arranged only between photosensitive pixel unit groups 21 that are distributed left and right (not shown in the drawings). Additionally, it can be arranged between some vertically distributed photosensitive pixel unit groups 21, and/or, some left-and-right distributed photosensitive pixel unit groups 21 (not shown in the drawings). In the present disclosure, by arranging the gap region 30 between at least two photosensitive pixel unit groups 21, and allowing the light beams above the gap region 30 to be received by at least one photosensitive pixel unit 211, the collection area of biometric information can be expanded. For instance, in one feasible embodiment, the gap region 30 can be configured for the arrangement of circuit signal lines to collect electrical signals. In another feasible embodiment, the gap region 30 can be configured for the arrangement of circuit components on it. By arranging a gap region 30 between at least two photosensitive pixel unit groups 21 and arranging circuit signal lines in the gap region, there is no need to arrange a wiring region on the optical sensor 20, thereby saving the structural size of the optical sensor 20.

Because the gap region 30 provided in the embodiment is arranged between at least two photosensitive pixel unit groups 21, to a certain extent, the circuit signal lines and/or circuit components in the present disclosure can minimize the occupation to the overall area of the optical sensor 20. This, in turn, saves more area for arranging photosensitive pixel unit 211, effectively reducing the area of the photosensitive region of the optical sensor 20 without increasing the collection area of biometric information on the display screen 40. It leads to cost saving and maximizes the utilization of the structural size for the bio-information recognition module, thus saving more internal space for electronic devices that use the bio-information recognition module according to the embodiment of the present disclosure.

In the embodiments of the present disclosure, the arrangement of the number and position of the gap regions 30 is not specifically limited. For example, gap region 30 can be arranged between any two adjacent photosensitive pixel unit groups 21, thereby forming a grid-like pattern composed of gap regions 30 across the entire optical sensor 20 in both horizontal and vertical directions. It can also be formed by the multiple gap regions 30 formed continuously in the same or parallel directions, or they can be various combinations of shapes of the multiple gap regions 30 formed in other regular or irregular ways.

In one feasible embodiment of the present disclosure, the width of the gap region 30 can be between 10 μm and 30 μm. For example, the width of the gap region 30 can be 10 μm, 15 μm, 20 μm, 25 μm, or 30 μm, etc. The present disclosure will not enumerate them all. Specifically, the number, position, shape, and dimension of the gap regions 30 can be determined by those skilled in the art based on the specific requirements for arranging the circuit signal lines and/or circuit components.

Furthermore, in FIG. 4, the photosensitive pixel unit group 21 is arranged in a matrix form, and correspondingly, the shape of the aforementioned gap region 30 is rectangular. It should be understood that the rectangular gap region 30 is just one scenario presented corresponding to the matrix-arranged photosensitive pixel units 211 and is not the only restriction on the shape of the gap region 30 in the present disclosure or the only solution that the embodiments of the present disclosure can support. The shape of the gap region 30 should be related to the arrangement of multiple photosensitive pixel unit groups 21, and the specific shape will depend on the actual circumstances. The present disclosure does not impose any restrictions.

Optionally, the gap region 30 can be formed on the optical sensor 20 as at least one strip-shaped region or at least one horizontal-and-vertical cross-connect region. As shown in FIG. 3, FIG. 3 is the first schematic structural diagram of the optical sensor 20. In this case, the gap region 30 is a horizontal-and-vertical cross-connect region formed on the optical sensor 20. As shown in FIG. 4, FIG. 4 is the second schematic structural diagram of the optical sensor 20. In this case, the gap region 30 is a strip-shaped region formed on the optical sensor 20. Certainly, in other embodiments, the aforementioned gap region 30 can also be formed as multiple horizontal-and-vertical cross-connect regions on the optical sensor 20, or as multiple strip-shaped regions on the optical sensor 20. Examples of the way of formation of the gap region 30 have been described in the foregoing description and will not be enumerated here.

In addition, in one optional embodiment of the present disclosure, the above-mentioned gap region 30 can comprise a first reserved region configured for arranging circuit signal lines; and/or, the above-mentioned gap region 30 can further comprise a second reserved region configured for arranging circuit components. For example, when the gap region 30 is a horizontal-and-vertical cross-connect region formed on the optical sensor 20, respectively, the first reserved region and the second reserved region can be a region arranged horizontally and a region arranged vertically; when the gap region 30 has multiple horizontal-and-vertical cross-connect regions formed on the optical sensor 20, the first reserved region can be arranged on a region that crosses horizontally and vertically, and the second reserved region can be arranged on another region that crosses horizontally and vertically; when the gap region 30 is a strip-shaped region formed on the optical sensor 20, the first reserved region and the second reserved region can be different positions within the strip-shaped region; and when the gap region 30 has multiple strip-shaped regions formed on the optical sensor 20, the first reserved region can be arranged on one strip-shaped region, and the second reserved region can be arranged on another strip-shaped region.

In the embodiments of the present disclosure, the light beams carrying bio-information above the gap region 30 can pass through the optical channels 11 and be received by at least one photosensitive pixel unit 211. Thus, the gap region 30, as arranged in the present disclosure, does not affect the normal reception of light beams carrying bio-information located above it (that is, light beams carrying bio-information located above the gap region 30 can be received by at least one photosensitive pixel unit 211). As a result, the bio-information recognition module provided in the present disclosure can effectively reduce the area of the photosensitive region of the optical sensor 20 without increasing the collection area of biological information on the display screen 40, thereby reducing the volume of the optical sensor 20 and lowering the cost of the bio-information recognition module.

Figure 6:
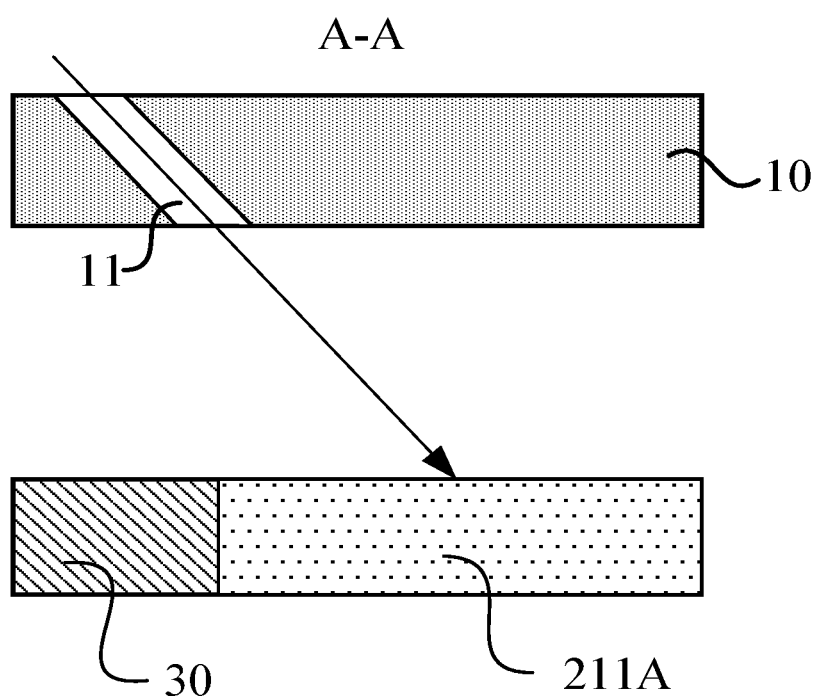
FIG. 6 is a sectional view at B-B in FIG. 3.

Referring to FIG. 6, FIG. 6 is a sectional view at the A-A position shown in FIG. 3. As can be seen by FIGS. 3 and 6, the light beams carrying bio-information located above the gap region 30 can be received by at least one photosensitive pixel unit 211 through the optical channel 11. It should be noted that FIGS. 3 and 6 represent just one situation in the embodiment of the present disclosure. By tilting the optical channels 11, the light beams carrying bio-information located above the gap region 30 that is horizontally arranged are received by a specific photosensitive pixel unit 211 of the photosensitive pixel unit group 21 (corresponding to FIG. 3, i.e., the photosensitive pixel unit 211g of the photosensitive pixel unit group 21 in the form of 3*3). In other embodiments, the light beams carrying bio-information located above the gap region 30 that is horizontally arranged can also be received by one or more photosensitive pixel units 211 of the photosensitive pixel unit group 21 near the center.

In conclusion, the bio-information recognition module provided in the embodiments of the present disclosure comprises an optical path guiding layer 10 and an optical sensor 20. The optical path guiding layer 10 comprises multiple optical channels 11, and the optical sensor 20 comprises multiple photosensitive pixel units 211, with adjacent at least two photosensitive pixel units 211 forming a photosensitive pixel unit group 21. The bio-information recognition module further comprises a gap region 30 provided between at least two photosensitive pixel unit groups 21. Light beams carrying bio-information above the gap region 30 are received by at least one photosensitive pixel unit 211 through the optical channels 11. This way, in usage, light beams carrying bio-information can be transmitted through multiple optical channels 11 to the optical sensor 20, where they are received and recognized by the photosensitive pixel units 211 of the optical sensor 20. Simultaneously, light beams carrying bio-information above the gap region 30 can also be received by at least one photosensitive pixel unit 211 through the optical channels 11, and their normal transmission remains unaffected. The present disclosure, by arranging the gap region 30 between at least two photosensitive pixel unit groups 21 and ensuring that light beams carrying bio-information above the gap region 30 are received by at least one photosensitive pixel unit 211 through the optical channels 11, on one hand, allows a larger area range of light beams carrying bio-information to enter the optical sensor 20, which effectively increases the bio-information collection area of the display screen 40 without changing the total area of photosensitive pixel unit 211 (i.e., the area of the photosensitive region). This, in turn, enables the bio-information recognition module to receive more optical signals of light beams carrying bio-information. In turn, more bio-information is obtained, thus contributing to the accuracy of bio-information recognition. On the other hand, without the need to increase the bio-information collection area of the display screen 40, the present disclosure can improve the effective utilization rate of the total area of photosensitive pixel units 211 (i.e., the area of the photosensitive region) in the optical sensor 20. This reduces the area of the photosensitive region of the optical sensor 20, thus reducing the size of the optical sensor 20. This, in turn, saves more internal space for electronic devices using the bio-information recognition module provided by the present disclosure while lowering the cost of the bio-information recognition module.

Referring to FIG. 2, in one of the feasible embodiments of the present disclosure, the optical channels 11 of the optical path guiding layer 10 can comprise inclined optical channels 111, wherein the inclined optical channels 111 form an angle θ with the straight line that is perpendicular to a surface of the optical sensor 20. In this way, with the area of the photosensitive region of the optical sensor 20 remaining unchanged, since the optical channel 11 comprises the inclined optical channels 111, the light beams carrying bio-information located on the outside of the display screen 40 (i.e., in a region other than the region of the display screen 40 that is directly opposite to the optical sensor 20) is also able to be incident on the photosensitive region of the optical sensor 20 due to the guiding effect of the inclined optical channel 111, thereby causing the incident range of the light beams carrying bio-information to be enlarged, and thus enabling the optical sensor 20 to receive light beams carrying biological information from a larger area above it as much as possible. As can be intuitively seen from the direction shown in FIG. 2, the photosensitive pixel unit group 21 of the bio-information recognition module provided in the embodiment can receive the light beams carrying bio-information located above the gap region. Clearly, by arranging the optical channels 11 as inclined optical channels 111, the present disclosure enables the optical sensor 20 to receive a larger area of biological information than the collection area of its own photosensitive region.

For example, the angle θ between the inclined optical channel 111 and the straight line perpendicular to the surface of the optical sensor 20 can be between 0° and 45°. For example, the angle θ between the inclined optical channel 111 and the straight line perpendicular to the surface of the optical sensor 20 can be 0°, 2°, 5°, 10°, 15°, 30°, 40°, or 45°, etc.

It should be noted that, in addition to the inclined optical channel 111, the optical channels 11 in the optical path guiding layer 10 can also comprise optical channels 11 that are not inclined. For instance, it can be arranged so that the inclined optical channel 111 located at the center of the optical path guiding layer 10 has an angle θ of 0° with the straight line perpendicular to the surface of the optical sensor 20. In other words, it can be considered that the optical channel 11 at this position is not in an inclined state and does not have the angle θ. For example, in one embodiment, among the multiple optical channels 11 corresponding to the photosensitive pixel unit group 21, the angle θ of the inclined optical channel 111 arranged in a straight-line direction from the optical channel 11 at the center to the optical channel 11 away from the center can be set in an increasing form.

Figure 13:
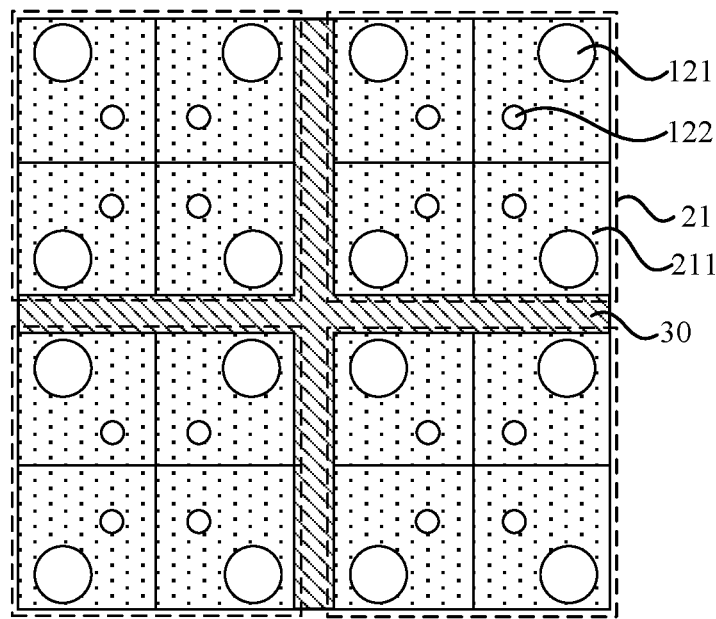
FIG. 13 is the first semi-perspective schematic diagram where diaphragm openings are mapped onto the optical sensor in the bio-information recognition module provided by the embodiments of the present disclosure.
Figure 14:
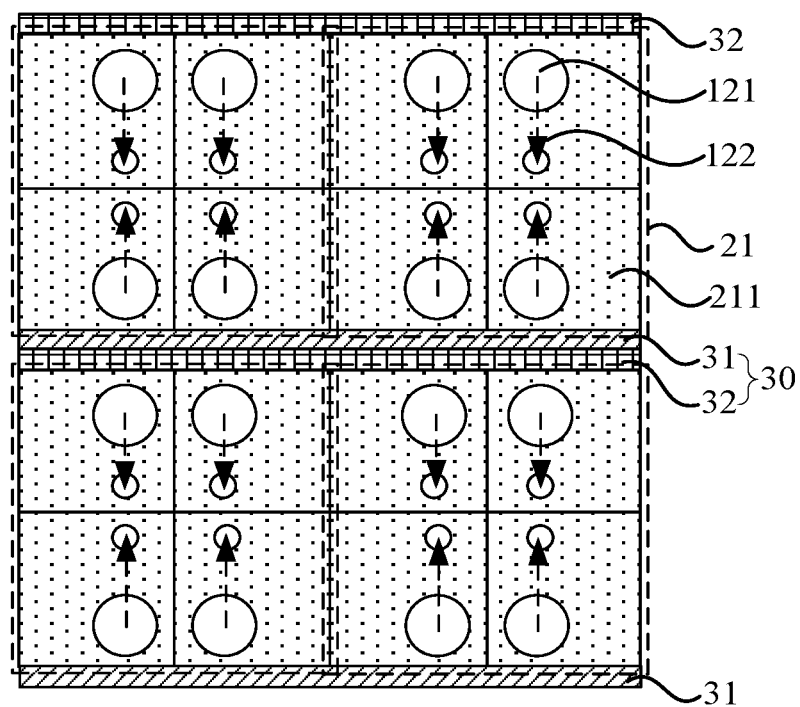
FIG. 14 is the second semi-perspective schematic diagram where diaphragm openings are mapped onto the optical sensor in the bio-information recognition module provided by the embodiments of the present disclosure.
Figure 15:
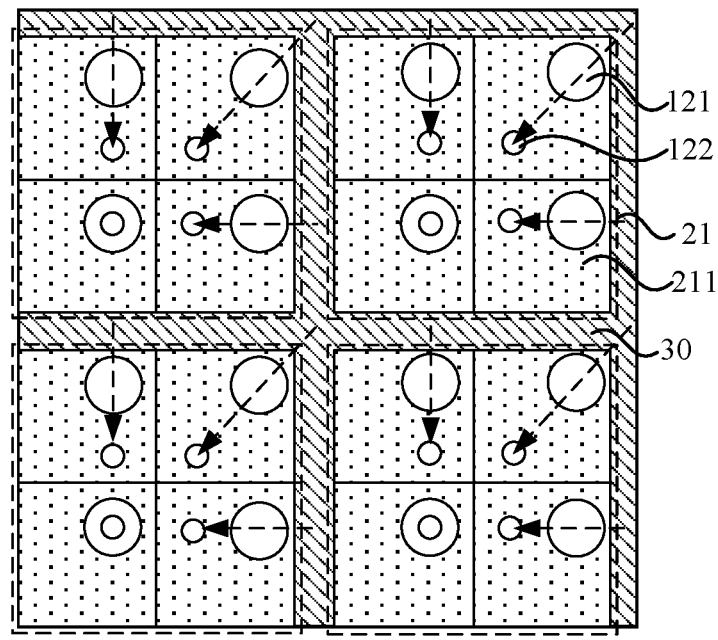
FIG. 15 is the third semi-perspective schematic diagram where diaphragm openings are mapped onto the optical sensor in the bio-information recognition module provided by the embodiments of the present disclosure.

Here, it is noted that the present disclosure does not limit the manner in which the optical channel 11 is formed. For example, the optical channel 11 can be composed of collimating apertures. Furthermore, the optical channel 11 can be composed of at least two layers of diaphragm openings. Additionally, the optical channel 11 can be composed of micro lenses and at least two layers of diaphragm openings. Referring to FIG. 1 and FIGS. 13 to 15, the drawings illustrate the schematic structure of the upper and lower sections of the optical channel 11 mapped onto the optical sensor 20. It should be noted that in FIG. 1 and FIGS. 13 to 15, the large circles represent the upper section of the optical channel 11, which can be the diaphragm openings on the top layer, for example. The small circles in the drawings represent the lower section of the optical channel 11, which can be the diaphragm openings on the bottom layer, for example. In FIGS. 14 and 15, the dashed lines with arrows represent the direction of light beam transmission (i.e., the light beams are transmitted toward the center of the photosensitive pixel unit group 21).

Preferably, the center of the lowest layer of diaphragm openings can be aligned with the center of the pixel unit without being limited to the examples shown in the drawings. It should be understood that in the embodiments of the present disclosure, the optical channel 11 is only provided as an example in the form with a large upper part and small lower part (i.e., a large upper sectional aperture and a small lower sectional aperture) and should not be viewed as the sole limitation on the shape of the optical channel 11 of the present disclosure. For example, in other feasible embodiments, the aperture of the optical channel 11 can be consistent up and down.

In a feasible embodiment of the embodiments of the present disclosure, the photosensitive pixel unit 211 can comprise a first photosensitive pixel unit 211A, wherein the first photosensitive pixel unit 211A receives light beams above the gap region 30 adjacent to the first photosensitive pixel unit 211A through the inclined optical channel 111.

Referring to FIG. 3 and FIG. 6, taking an example of multiple photosensitive pixel units 211 that compose the photosensitive pixel unit group 21 in a 3*3 pattern, the first photosensitive pixel unit 211A is the photosensitive pixel unit 211g in the photosensitive pixel unit group 21. In this case, the first photosensitive pixel unit 211A can receive the light beams above the horizontal direction of the gap region 30. It should be noted that when the first photosensitive pixel unit 211A is the photosensitive pixel unit 211i in the photosensitive pixel unit group 21, the first photosensitive pixel unit 211A can receive the light beams above the gap region 30 in the horizontal direction, as shown in FIG. 3, and it can also receive the light beams above the gap region 30 in the vertical direction.

When the bio-information recognition module comprises only a strip-shaped region, the first photosensitive pixel unit 211A can receive the light beams above the gap region 30 adjacent to the first photosensitive pixel unit 211A through the inclined optical channels 111. An example is provided in which multiple photosensitive pixel units 211 forming the photosensitive pixel unit group 21 are combined in the pattern of 2*4 as shown in FIG. 5. Assuming that the first photosensitive pixel unit 211A is the photosensitive pixel unit 211j of the photosensitive pixel unit group 21, the first photosensitive pixel unit 211A can receive the light beams above the gap region 30 (i.e., the second gap region 32 as shown in FIG. 5); and assuming that the first photosensitive pixel unit 211A is the photosensitive pixel unit 211n of the photosensitive pixel unit group 21, the first photosensitive pixel unit 211A can receive the light beams above the gap region 30 (i.e., the first gap region 31 as shown in FIG. 5) below it.

When the bio-information recognition module comprises at least a horizontal-and-vertical cross-connect region, the first photosensitive pixel unit 211A can receive, via the inclined optical channel 111, the light beams above one or more of the gap regions 30 adjacent to the first photosensitive pixel unit 211A. An example is provided in which multiple photosensitive pixel units 211 forming the photosensitive pixel unit group 21 are combined in the pattern of 3*3 as shown in FIG. 3. Assuming that the first photosensitive pixel unit 211A is the photosensitive pixel unit 211v of the photosensitive pixel unit group 21, the first photosensitive pixel unit 211A can receive the light beams above the gap region 30 above it and/or above the gap region 30 on the right.

Figure 9:
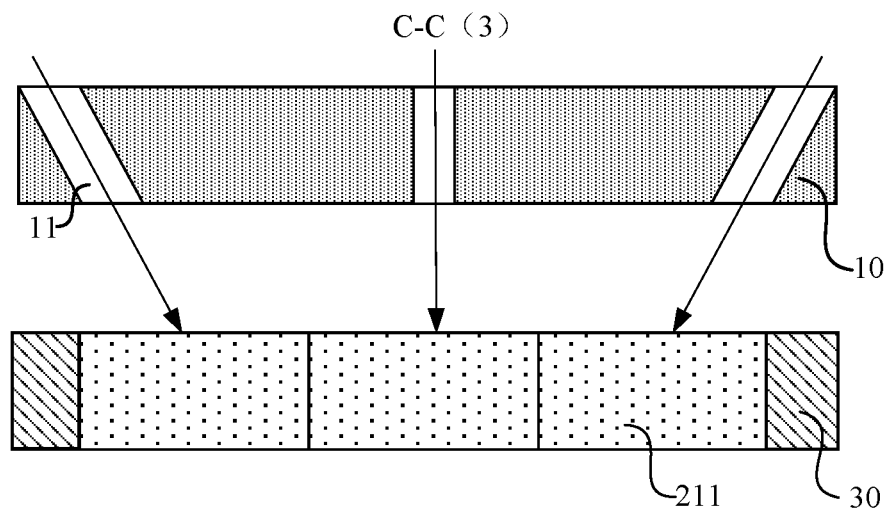
FIG. 9 is the third sectional view at C-C in FIG. 3.

Additionally, referring to FIG. 9, in one embodiment of the embodiments of the present disclosure, the inclined optical channel 111 corresponding to the first photosensitive pixel unit 211A can be tilted toward the center of the photosensitive pixel unit group 21 along the direction of the light beams. As a result, all light beams carrying bio-information can be tilted toward the center of the photosensitive pixel unit group 21, thus increasing the light beams incident on the photosensitive region of the optical sensor 20 as much as possible. Furthermore, because the optical sensor 20 does not require a dedicated wire routing region due to the routing and other arrangement of the lines through the gap region 30, the area of the optical sensor 20 can also be relatively reduced, thus reducing the overall volume of the module.

The inclined optical channel 111 corresponding to the first photosensitive pixel unit 211A can tilt towards the center of the photosensitive pixel unit group 21 in the direction of the light beams, which can comprise various scenarios. For example, when the gap region 30 comprises only strip-shaped regions, the center mentioned above can be the central axis of the photosensitive pixel unit group 21. For example, as shown in FIG. 14, it is to be noted that the dashed lines with arrowheads in FIG. 14 represent the direction of light beam transmission, wherein the light beam is toward the center of the photosensitive pixel unit group 21. The larger-diameter circular hole in FIG. 14 represents the cross section of the end of the optical channel 11 away from the optical sensor 20, and the smaller-diameter circular hole represents the section of the end of the optical channel 11 near the optical sensor 20. In this case, the first photosensitive pixel unit 211A (assuming that it is the first photosensitive pixel unit 211 on the left of the first row in each photosensitive pixel unit group 21) corresponds to the inclined optical channel 111, which is tilted in the direction of the horizontal central axis of the photosensitive pixel unit group 21 along the direction of the light beam. For example, when the first photosensitive pixel unit 211 on the left of the first row in each photosensitive pixel unit group 21 serves as the first photosensitive pixel unit 211A for that photosensitive pixel unit group 21, the light beams from the gap region (i.e., the second gap region 32) above the first photosensitive pixel unit 211A is received by the first photosensitive pixel unit 211A. For example, when the first photosensitive pixel unit 211 on the left of the second row in each photosensitive pixel unit group 21 serves as the first photosensitive pixel unit 211A for that photosensitive pixel unit group 21, the light beams from the lower portion of the gap region (i.e., the first gap region 31) below the first photosensitive pixel unit 211A are received by the first photosensitive pixel unit 211A.

For another example, when the gap region 30 comprises at least one horizontal-and-vertical cross-connect region, as illustrated in FIG. 15, in this case, the inclined optical channel 111 corresponding to the first photosensitive pixel unit 211A can tilt along the horizontal center axis of the photosensitive pixel unit group 21 in the direction of the light beam (assuming that the first photosensitive pixel unit 211A is the first photosensitive pixel unit 211 on the left side of the first row of each photosensitive pixel unit group 21). The inclined optical channel 111 corresponding to the first photosensitive pixel unit 211A can also tilt in the direction of the light beam toward the geometric center of the photosensitive pixel unit group 21 (assuming that the first photosensitive pixel unit 211A is the first photosensitive pixel unit 211 on the right side of the first row of each photosensitive pixel unit group 21). The inclined optical channel 111 corresponding to the first photosensitive pixel unit 211A can further tilt in the direction of the light beam toward the vertical center axis of the photosensitive pixel unit group 21 (assuming that the first photosensitive pixel unit 211A is the first photosensitive pixel unit 211 on the right side of the second row of each photosensitive pixel unit group 21).

In another feasible embodiment, optionally, the photosensitive pixel unit 211 can comprise a first photosensitive pixel unit 211A, wherein the first photosensitive pixel unit 211A receives light beams above the gap region 30 adjacent to other photosensitive pixel units 211, excluding the first photosensitive pixel unit 211A, through the inclined optical channel 111.

Figure 11:
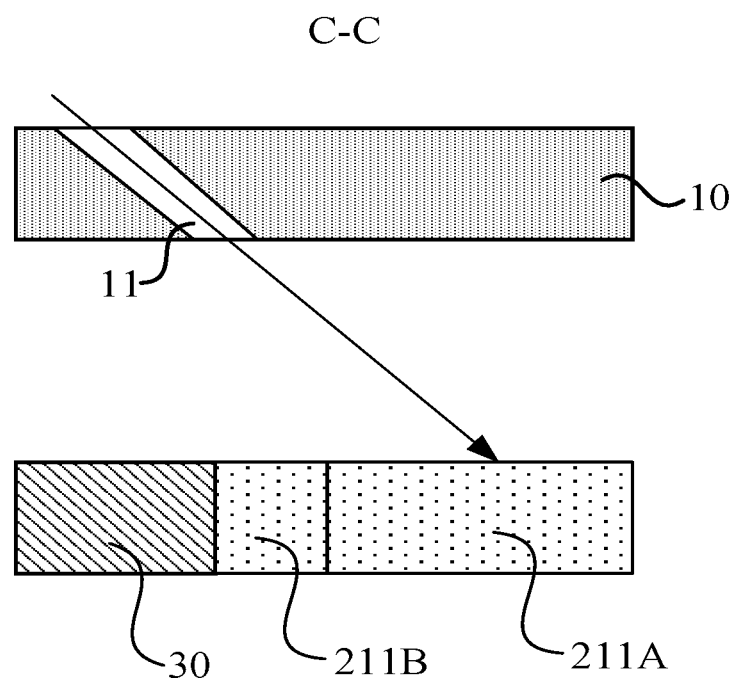
FIG. 11 is a sectional view at D-D in FIG. 2.

In other words, the first photosensitive pixel unit 211A can receive the light beams above the gap region 30 from the adjacent other photosensitive pixel unit 211B, excluding itself, through the inclined optical channel 111. Referring to FIG. 3 and FIG. 11, when the first photosensitive pixel unit 211A is one of the photosensitive pixel units 211 in the 3*3 pattern of the photosensitive pixel unit group 21, assuming that the first photosensitive pixel unit 211A is the photosensitive pixel unit 211*i*, then the first photosensitive pixel unit 211A can receive the light beams above the gap region 30 adjacent to the photosensitive pixel unit 211*h*. It should be understood that the first photosensitive pixel unit 211A receiving light beams above the gap region 30 adjacent to the photosensitive pixel unit 211*h* is just one example in the present disclosure. However, it is not a specific limitation on the light beams received above the gap region 30 by another adjacent photosensitive pixel unit 211 when the photosensitive pixel unit 211*i* serves as the first photosensitive pixel unit 211A. For instance, in other embodiments, when the first photosensitive pixel unit 211A is the photosensitive pixel unit 211*i*, the first photosensitive pixel unit 211A can also receive light beams above the gap region 30 that is adjacent to photosensitive pixel unit 211*f*, light beams above the gap region 30 that is adjacent to photosensitive pixel unit 211*g*, and so on. The present disclosure does not list each possibility individually.

In some embodiments of the present disclosure, the other photosensitive pixel units 211, apart from the first photosensitive pixel unit 211A mentioned above, can comprise a photosensitive pixel unit 211 positioned on the opposite side of the first photosensitive pixel unit 211A within the same photosensitive pixel unit group 21. It should be noted that the photosensitive pixel units 211 on the opposite side comprise a photosensitive pixel unit 211 that is in mirror symmetry with the first photosensitive pixel unit 211A in the vertical direction; a photosensitive pixel unit 211 that is in mirror symmetry with the first photosensitive pixel unit 211A in the horizontal direction; and a photosensitive pixel unit 211 that is diagonal to the first photosensitive pixel unit 211A. For example, taking the first photosensitive pixel unit 211A as one of the photosensitive pixel units 211 of the photosensitive pixel unit group 21 in the 3*3 pattern shown in FIG. 3 (for ease of description, assuming that the first photosensitive pixel unit 211A is photosensitive pixel unit 211*a*), in this case, the first photosensitive pixel unit 211A can receive light beams above the gap region 30 adjacent to the photosensitive pixel unit 211*g* that is in mirror symmetry with the photosensitive pixel unit 211*a* in the vertical direction. Alternatively, the first photosensitive pixel unit 211A can receive the light beams above the gap region 30 adjacent to the photosensitive pixel unit 211*c* that is in mirror symmetry with the first photosensitive pixel unit 211*a* in the horizontal direction. Alternatively, the first photosensitive pixel unit 211A can receive the light beams above the gap region 30 adjacent to the photosensitive pixel unit 211*i* which is diagonal to the first photosensitive pixel unit 211*a*.

It can comprise the photosensitive pixel unit 211 (photosensitive pixel unit 211*b*) above the first photosensitive pixel unit 211A; the photosensitive pixel unit 211 (photosensitive pixel unit 211*h*) below the first photosensitive pixel unit 211A; the photosensitive pixel unit 211 (photosensitive pixel unit 211*d*) to the left of the first photosensitive pixel unit 211A; the photosensitive pixel unit 211 (photosensitive pixel unit 211*f*) to the right of the first photosensitive pixel unit 211A; and the photosensitive pixel unit 211 (photosensitive pixel unit 211*g*, first photosensitive pixel unit 211*c*, first photosensitive pixel unit 211*a*, and first photosensitive pixel unit 211*i*) that is diagonal to the first photosensitive pixel unit 211A.

In one embodiment of the embodiments of the present disclosure, within the photosensitive pixel unit group 21, the inclined optical channels 111, corresponding to the two photosensitive pixel units 211 that are symmetrically positioned with respect to the center of the photosensitive pixel unit group 21, can intersect above the center. Therefore, the first photosensitive pixel unit 211A receives, via the inclined optical channels 111, the light beams above the gap region 30 adjacent to the photosensitive pixel unit 211 that is centrally symmetrical to the first photosensitive pixel unit 211A in the same photosensitive pixel unit group 21.

Figure 7:
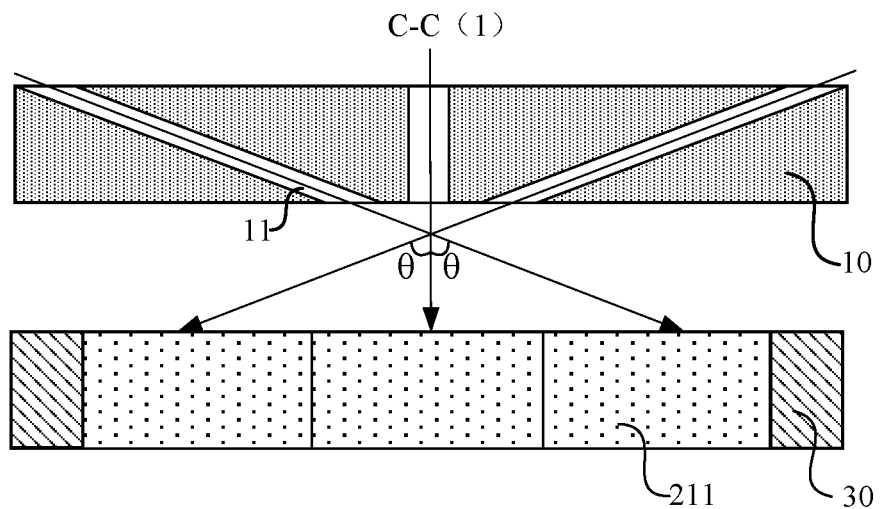
FIG. 7 is the first sectional view at C-C in FIG. 3.

Exemplarily, when two inclined optical channels 111 intersect above the center of the photosensitive pixel unit group 21, for better understanding, FIGS. 3 and 7 are referred to. In one possible implementation, the embodiment takes multiple photosensitive pixel units 211 forming the photosensitive pixel unit group 21 to be combined in the pattern of 3*3, with taking the example that two photosensitive pixel units 211 symmetrical with respect to the center of the photosensitive pixel unit group 21 are respectively photosensitive pixel unit 211*d* and photosensitive pixel unit 211*f*. A schematic view of the structure as described in FIG. 7 can be obtained in a plane section where the connecting line of the two photosensitive pixel units 211 is located. At this time, the inclined optical channels 111 corresponding to the two photosensitive pixel units 211 intersect above the center of the photosensitive pixel unit group 21. When multiple photosensitive pixel units 211 forming the photosensitive pixel unit group 21 are combined in the pattern of 3*3, light beams above the gap region 30 adjacent to the photosensitive pixel unit 211*d* can be received by the photosensitive pixel unit 211*f* through the corresponding inclined optical channels 111; and light beams above the gap region 30 adjacent to the photosensitive pixel unit 211*f* can be received by the photosensitive pixel unit 211*d* through the corresponding inclined optical channels 111.

Figure 8:
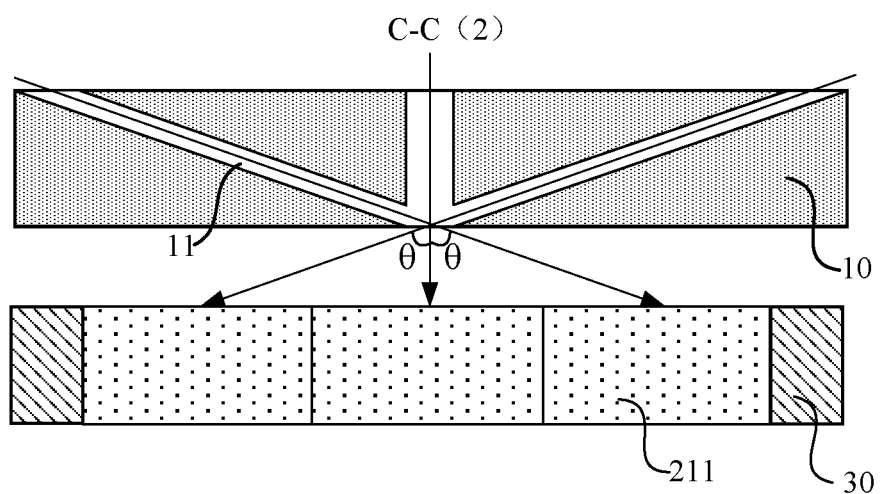
FIG. 8 is the second sectional view at C-C in FIG. 3.

Exemplarily, in another possible implementation, it is also possible for the two inclined optical channels 111 to form an overlapping region within the optical path guiding layer 10, as shown for ease of understanding with reference to FIGS. 3 and 8. Continuing with the example of two photosensitive pixel units 211 that are symmetrical relative to the center of the photosensitive pixel unit group 21, namely, photosensitive pixel unit 211*d* and photosensitive pixel unit 211*f*, a schematic view of the structure as described in FIG. 8 can be obtained in a plane section where the connecting line of the two photosensitive pixel units 211 is located. At this time, the inclined optical channels 111 corresponding to the two photosensitive pixel units 211 intersect above the center of the photosensitive pixel unit group 21 within the optical path guiding layer 10. It should be noted that in FIG. 8, the optical path guiding layer 10 is a thicker layer where the optical channels 11 are fully formed. If the optical path guiding layer 10 comprises multiple light-shielding layers, the intersection points of the inclined optical channels 111 can also be positioned between two light-shielding layers.

In the embodiment, within the photosensitive pixel unit group 21, the inclined optical channels 111, corresponding to the two photosensitive pixel units 211 that are symmetrically positioned with respect to the center of the photosensitive pixel unit group 21, is able to not intersect above the center. For example, for ease of comparative understanding, referring to FIGS. 3 and 9, two photosensitive pixel units 211 that are symmetrically positioned relative to the center of the photosensitive pixel unit group 21 each receive the light beams above gap region 30 adjacent to the two photosensitive pixel units themselves through their respective corresponding inclined optical channels 111, rather than receiving the light beams above the gap region 30 adjacent to each other. Of course, this scenario is just one form provided in the present disclosure where the inclined optical channels 111 corresponding to two photosensitive pixel units 211 that are centrally symmetrical relative to the photosensitive pixel unit group 21, within the photosensitive pixel unit group 21, do not intersect above the center. It should not be considered as a limitation of the present disclosure.

In one embodiment of the embodiments of the present disclosure, in multiple inclined optical channels 111 corresponding to one photosensitive pixel unit group 21, angles of the two inclined optical channels 111 that are symmetric with respect to the center of the photosensitive pixel unit group 21 can be the same. For example, as shown in FIG. 3 and FIG. 7, when multiple photosensitive pixel units 211 forming the photosensitive pixel unit group 21 are combined in a pattern of 3*3, the inclined optical channel 111 corresponding to photosensitive pixel unit 211$d$ and the inclined optical channel 111 corresponding to photosensitive pixel unit 211$f$ each have an equal angle with a straight line perpendicular to the surface of the optical sensor 20.

Exemplarily, in another embodiment, in multiple inclined optical channels 111 corresponding to one photosensitive pixel unit group 21, angles of the inclined optical channels 111 that correspond to the photosensitive pixel units 211 equidistant from the center of the photosensitive pixel unit group 21 can be the same.

Taking the example of multiple photosensitive pixel units 211 that form the photosensitive pixel unit group 21 arranged in a 3*3 pattern, as shown in FIG. 3, part from the inclined optical channel 111 corresponding to photosensitive pixel unit 211$e$, the inclined optical channels 111 corresponding to the other photosensitive pixel units 211 have angles $\theta$ with respect to the centerline of the light-sensitive pixel unit group 21, in which the angles are equal. When the photosensitive pixel unit group 21 is arranged in other patterns, those skilled in the art can similarly derive the same, and therefore, the present disclosure will not further elaborate.

Exemplarily, in another embodiment, in multiple inclined optical channels 111 corresponding to one photosensitive pixel unit group 21, an angle of the inclined optical channels 111 that are closer to the center of the photosensitive pixel unit group 21 can be smaller than or equal to an angle $\theta$ of the inclined optical channels 111 that are farther from the center of the photosensitive pixel unit group 21.

Figure 10:
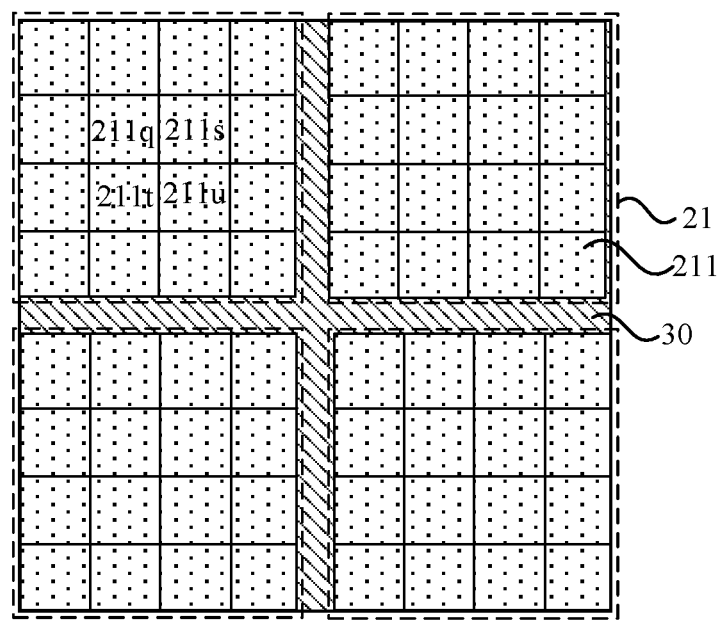
FIG. 10 is the fourth schematic structural diagram of the optical sensor in the bio-information recognition module provided by the embodiments of the present disclosure.

Referring to FIG. 2, for photosensitive pixel unit groups 211 closer to the center of the photosensitive pixel unit group 21, the angle $\theta$ between their corresponding inclined optical channels 111 and the centerline of the photosensitive pixel unit group 21 is smaller; conversely, the angle $\theta$ is larger. In the case of a 4*4 pattern of multiple photosensitive pixel units 211 forming the photosensitive pixel unit group 21, as shown in FIG. 10, the angles $\theta$ between the inclined optical channels 111 corresponding to photosensitive pixel unit 211$r$, photosensitive pixel unit 211$s$, photosensitive pixel unit 211$t$, and photosensitive pixel unit 211$u$ of the photosensitive pixel unit group 21, and the centerline of the photosensitive pixel unit group 21, are smaller than the angles $\theta$ between the inclined optical channels 111 corresponding to other photosensitive pixel units 211B of the photosensitive pixel unit group 21 and the centerline of the photosensitive pixel unit group 21. It should be noted that the tilt angles of the inclined optical channels 111 for each photosensitive pixel unit group 21 can be consistent. In other words, each photosensitive pixel unit group 21 can be identical (shown with reference to FIG. 2).

Figure 12:
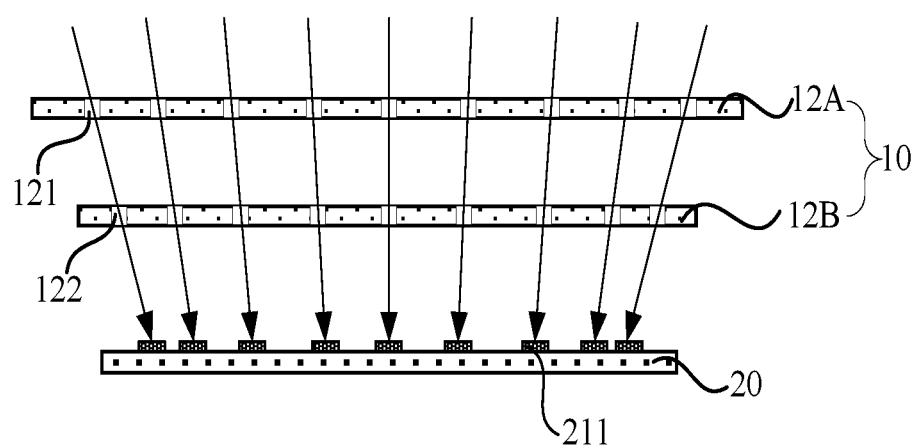
FIG. 12 is the second schematic structural diagram of the bio-information recognition module provided by the embodiments of the present disclosure.

Referring again to FIGS. 12 and 13 in conjunction, in an optional embodiment of the present disclosure, the optical path guiding layer 10 can comprise at least two layers of light-shielding layers that are provided at intervals. On the light-shielding layers, a diaphragm opening can be formed, and at least two diaphragm openings corresponding to the at least two layers of the light-shielding layers form at least a portion of the optical channels 11.

For ease of description and understanding, the at least two light-shielding layers described above can be subdivided into a first light-shielding layer 12A and a second light-shielding layer 12B. The diaphragm openings on the light-shielding layers can be divided into a first diaphragm opening 121 located on the first light-shielding layer 12A and a second diaphragm opening 122 located on the second light-shielding layer 12B. When the light-shielding layer comprises more than two layers, the division continues in the same way. The following examples in the embodiment will be illustrated by way of an example in which the light-shielding layers are in two layers. The light beams carrying bio-information can be sequentially incident on the optical sensor 20 through the first diaphragm opening 121 of the first light-shielding layer 12A and the second diaphragm opening 122 of the second light-shielding layer 12B, and thus be received by the photosensitive pixel unit 211 on the optical sensor 20.

It should be understood that the light-shielding layer is provided to facilitate directing the light beams carrying bio-information to be incident on the photosensitive region of the optical sensor 20 from the diaphragm opening of the light-shielding layer. Specifically, the provision of the diaphragm openings can be based on the degree of inclination of the optical channel 11, which is not limited by the present disclosure. Exemplarily, the above light-shielding layers can be in two, three, or four layers, etc., and the specific number of layers can be determined by those skilled in the art according to the actual situation.

Referring again to FIG. 13, FIG. 13 illustrates a schematic view of a structure of the first diaphragm opening 121 and the second diaphragm opening 122 projected on the optical sensor 20 when the light-shielding layer comprises two layers. It is noted that the first diaphragm opening 121 illustrated in FIG. 13 is an aperture provided on the first light-shielding layer 12A for guiding the passage of the light beam, and the second diaphragm opening 122 is an aperture provided on the second light-shielding layer 12B for guiding the passage of the light beam. In the embodiment, the aperture of the first diaphragm opening 121 is larger than the aperture of the second diaphragm opening 122. The second diaphragm opening 122, relative to the first diaphragm opening 121, is closer to the center region of the photosensitive pixel unit group 21. In this way, it can be achieved that, after light beams sequentially pass through the first diaphragm opening 121 and the second diaphragm opening 122, the light beams converge towards the center of the photosensitive pixel unit 211. In addition, the present disclosure does not impose any restrictions on the sectional shapes of the first diaphragm opening 121 and the second diaphragm opening 122. For example, the section of the first diaphragm opening 121 and the second diaphragm opening 122 can be one or more of circular, square, or any irregular shape, among others.

Figure 16:
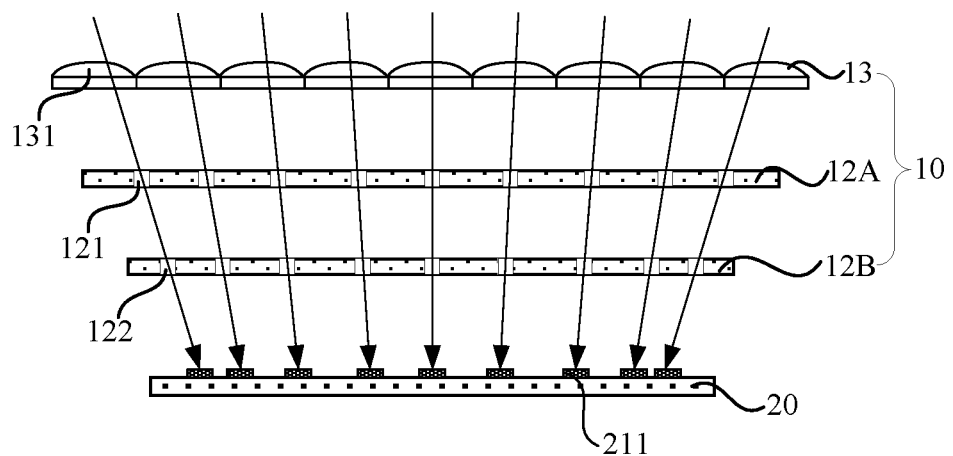
FIG. 16 is the third schematic structural diagram of the bio-information recognition module provided by the embodiments of the present disclosure.

Referring again to FIG. 16, in one embodiment of the embodiments of the present disclosure, the optical path guiding layer 10 can comprise a micro lens group arranged on the light-shielding layers 13. The micro lens group 13 can comprise multiple micro lens units 131, and the micro lens units 131 form at least a portion of the optical channels 11. In this way, the micro lens unit 131 and the diaphragm opening can together form the optical channel 11.

Additionally, the micro lens unit 131 is capable of providing a degree of convergence and guidance to the light beams carrying bio-information. In other words, the micro lens unit 131 is capable of converging as many light beams carrying bio-information as possible to be directed onto the photosensitive region of the optical sensor 20. The light beams carrying bio-information after converging through the micro lens unit 131 can be sequentially passed through the diaphragm openings of at least two light-shielding layers and then incident on the optical sensor 20, which are thereby received by the photosensitive pixel unit 211 of the optical sensor 20.

In one embodiment of the embodiments of the present disclosure, the light beams carrying bio-information can be received by one photosensitive pixel unit group 21 through one micro lens unit 131. That is, one micro lens unit 131 corresponds to one photosensitive pixel unit group 21.

Figure 17:
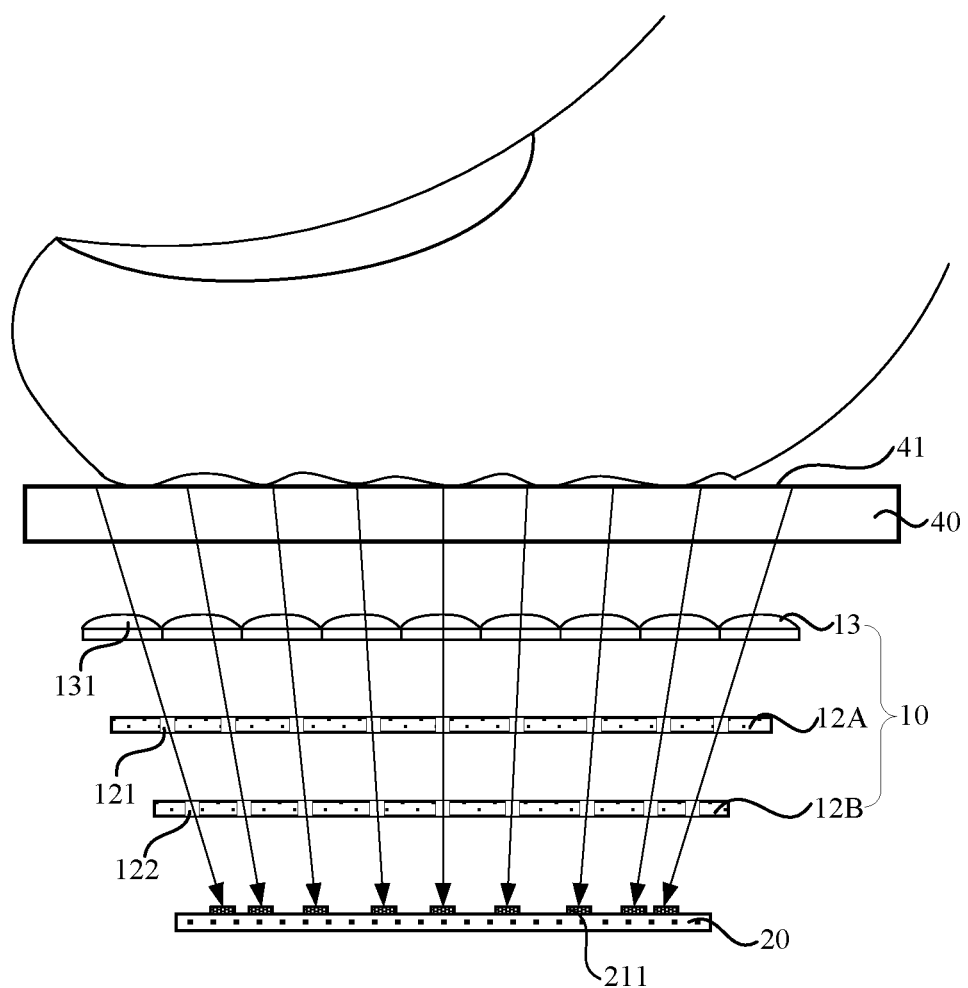
FIG. 17 is a schematic diagram of the structure of an electronic device provided by the embodiment of the present disclosure.

Referring again in conjunction with FIG. 17, in another aspect of the embodiments of the present disclosure, an electronic device is provided, wherein the electronic device can comprise a display screen 40 and a bio-information recognition module provided under the display screen 40, as described in any of the previous sections.

In this way, the user can place a carrier with individual biometric characteristics, such as a finger, palm, etc., to be attached to the bio-information recognition region 41 of the display screen 40. In the case of under-screen fingerprint recognition, for example, the light beams that are irradiated on and reflected from a finger pattern can carry the pattern characteristics of the irradiated finger position as fingerprint information. The light beams carrying the fingerprint information are incident on the optical sensor 20 after being guided and transmitted by the optical path guiding layer 10 in the bio-information recognition module. By receiving the light beams carrying bio-information above the gap region 30, the present disclosure enables the light beams carrying bio-information over a larger region to be incident on the optical sensor 20. Therefore, the electronic devices are enabled to receive more optical signals reflected from the fingerprint, thus obtaining more fingerprint information. In this way, without increasing the area of the bio-information recognition region 41 of the display screen 40, the pixel collection range of the optical sensor 20 can be effectively increased to improve the recognition accuracy of the bioinformation recognition. At the same time, it can reduce the manufacturing cost of electronic devices, reduce the size of the module, and save more internal space for electronic devices.

Figure 18:
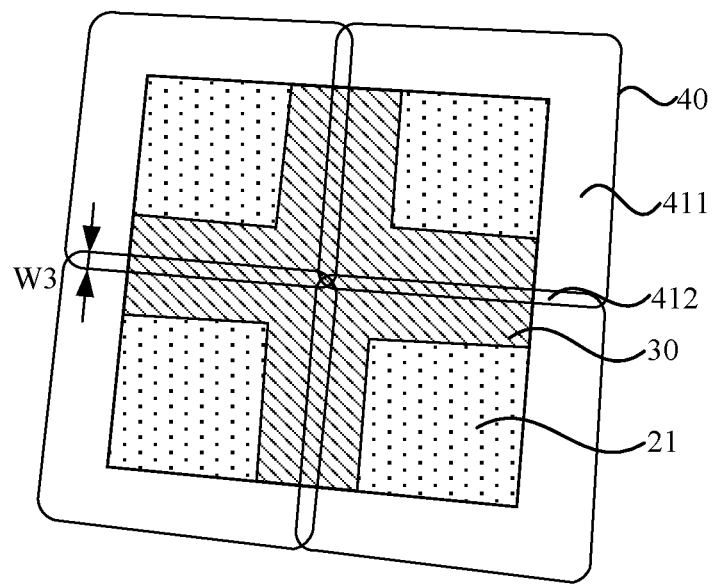
FIG. 18 is the semi-perspective schematic diagram showing the position relationship between the photosensitive pixel unit group and the gap region and the display screen when being transparent in the electronic device provided by the embodiments of the present disclosure.

With further reference to FIG. 18, in one embodiment of the embodiments of the present disclosure, a bio-information recognition region 41 can be provided on the display screen 40, and the bio-information recognition region 41 can be a fingerprint identification region. The bio-information recognition region 41 can comprise multiple sections 411 corresponding to multiple photosensitive pixel unit groups 21. The light beams carrying biological feature information from the sections 411 are received by the corresponding photosensitive pixel unit groups 21 through the optical channels 11. The number of the above-mentioned sections 411 is not limited, and it can comprise 2 sections 411, 3 sections 411, 4 sections 411 (as shown in FIG. 18), or 5 sections 411, among others. Further, the present disclosure does not limit the shape of the sections 411, which can be square or polygonal, for example. Optionally, the shape of the section 411 can correspond to the arrangement of the photosensitive pixel unit group 21 of the optical sensor 20. For example, if the photosensitive pixel unit group 21 is square, the shape of the sections 411 can be square; and if the photosensitive pixel unit group 21 is polygonal, the shape of the sections 411 can also be polygonal.

In order to obtain more light beams carrying bio-information, in one embodiment of the embodiments of the present disclosure, an area of orthographic projection of at least one section 411 on the optical sensor 20 can be greater than the area of its corresponding photosensitive pixel unit group 21. In this way, when the user places a carrier with individual biometric features in the bio-information recognition region 41 of the display screen 40, each section 411 can capture as much bio-information as possible, thus directing the light beams carrying that bio-information to the photosensitive region of the optical sensor 20.

In one embodiment of the embodiments of the present disclosure, orthographic projections of at least two adjacent sections 411 can have an overlapping region 412 on the optical sensor 20. That is, as shown in FIG. 18, two adjacent sections 411 are provided with an overlapping region 412. In this way, it can prevent situations where the light beams carrying bio-information between two sections 411 cannot be received by the optical sensor 20, thereby increasing the collection range of light beams carrying bio-information.

To avoid waste of area due to a too large overlapping region 412 or the occurrence of missed capture due to a too small overlapping region 412, in the embodiment, the overlapping region 412 described above can be rectangular, and the width W3 of the overlapping region can range from 3 to 5 micrometers. For example, the width W3 of the overlapping region can be 3 μm, 4 μm, 5 μm, and so on.

The above is only an embodiment of the present disclosure, which is not intended to limit the scope of protection of the present disclosure, and the present disclosure can have various changes and variations for those skilled in the art. Any modification, equivalent substitution, improvement, etc. made within the spirit and principles of the present disclosure shall be included in the scope of protection of the present disclosure.

INDUSTRIAL PRACTICALITY

The present disclosure provides a bio-information recognition module and an electronic device. The bio-information recognition module comprises an optical path guiding layer and an optical sensor. The optical path guiding layer comprises multiple optical channels, and the optical sensor comprises multiple photosensitive pixel units, with adjacent at least two photosensitive pixel units forming a photosensitive pixel unit group. The bio-information recognition module further comprises a gap region provided between at least two photosensitive pixel unit groups. Light beams carrying bio-information above the gap region are received by at least one photosensitive pixel unit through the optical channels. The electronic device comprises a display screen and a bio-information recognition module provided under the display screen. The bio-information recognition module and the electronic device are capable of receiving a larger region range of light beams carrying bio-information without increasing the overall volume of the module.

Furthermore, it can be understood that the bio-information recognition module and electronic device in the present disclosure are reproducible and can be applied in various industrial applications. For example, the bio-information recognition module and electronic device of the present disclosure can be applied in the field of electronic devices.

What is claimed is:

1. A bio-information recognition module, wherein the bio-information recognition module comprises an optical path guiding layer and an optical sensor; the optical path guiding layer comprises multiple optical channels, and the optical sensor comprises multiple photosensitive pixel units, with adjacent at least two photosensitive pixel units forming a photosensitive pixel unit group; and the bio-information recognition module further comprises a gap region provided between at least two photosensitive pixel unit groups; and light beams carrying bio-information above the gap region are received by at least one photosensitive pixel unit through the optical channels, wherein the optical channels comprise inclined optical channels, wherein the inclined optical channels form an angle with a straight line that is perpendicular to a surface of the optical sensor, wherein in multiple inclined optical channels corresponding to one photosensitive pixel unit group, angles of two inclined optical channels that are symmetric with respect to a center of the photosensitive pixel unit group are the same.

2. The bio-information recognition module according to claim 1, wherein the photosensitive pixel units comprise a first photosensitive pixel unit, wherein the first photosensitive pixel unit receives light beams above the gap region adjacent to the first photosensitive pixel unit through the inclined optical channels.

3. The bio-information recognition module according to claim 2, wherein the inclined optical channels corresponding to the first photosensitive pixel unit are tilted toward a center of the photosensitive pixel unit group along a direction of the light beams.

4. The bio-information recognition module according to claim 1, wherein the photosensitive pixel units comprise a first photosensitive pixel unit, wherein the first photosensitive pixel unit receives light beams above the gap region adjacent to other photosensitive pixel units, excluding the first photosensitive pixel unit, through the inclined optical channels.

5. The bio-information recognition module according to claim 4, wherein the other photosensitive pixel units, excluding the first photosensitive pixel unit, comprise a photosensitive pixel unit positioned on an opposite side of the first photosensitive pixel unit within the same photosensitive pixel unit group.

6. The bio-information recognition module according to claim 4, wherein within the photosensitive pixel unit group, the inclined optical channels corresponding to two photosensitive pixel units that are symmetric with respect to a center of the photosensitive pixel unit group intersect above the center.

7. The bio-information recognition module according to claim 1, wherein in the multiple inclined optical channels corresponding to the one photosensitive pixel unit group, angles of the inclined optical channels that correspond to the photosensitive pixel units equidistant from the center of the photosensitive pixel unit group are the same.

8. The bio-information recognition module according to claim 1, wherein in multiple inclined optical channels corresponding to one photosensitive pixel unit group, an angle of the inclined optical channels that are closer to a center of the photosensitive pixel unit group is smaller than or equal to an angle of the inclined optical channels that are farther from the center of the photosensitive pixel unit group.

9. The bio-information recognition module according to claim 1, wherein the optical path guiding layer comprises at least two layers of light-shielding layers that are provided at intervals; on the light-shielding layers, diaphragm openings are formed, and at least two diaphragm openings corresponding to the at least two layers of the light-shielding layers form at least a portion of the optical channels.

10. The bio-information recognition module according to claim 1, wherein the multiple photosensitive pixel units forming the photosensitive pixel unit group are combined in an N*M pattern, wherein N is an integer greater than or equal to 1, and M is an integer greater than or equal to 2.

11. The bio-information recognition module according to claim 1, wherein the gap region is formed on the optical sensor as at least one strip-shaped region or at least one horizontal-and-vertical cross-connect region.

12. The bio-information recognition module according to claim 1, wherein the gap region comprises a first reserved region configured for laying out circuit signal lines.

13. The bio-information recognition module according to claim 12, wherein the gap region further comprises a second reserved region configured for arranging circuit components.

14. An electronic device, wherein the electronic device comprises a display screen and the bio-information recognition module according to claim 1 provided under the display screen.

15. The electronic device according to claim 14, wherein a bio-information recognition region is arranged on the display screen; the bio-information recognition region comprises multiple sections corresponding to multiple photosensitive pixel unit groups; and light beams carrying biological feature information from the sections are received by corresponding photosensitive pixel unit groups through the optical channels.

16. The electronic device according to claim 15, wherein an area of orthographic projection of at least one section on the optical sensor is greater than an area of its corresponding photosensitive pixel unit group.

17. The electronic device according to claim 16, wherein orthographic projections of at least two adjacent sections on the optical sensor have an overlapping region.

18. The electronic device according to claim 17, wherein the overlapping region is rectangular, and a width of the overlapping region is between 3-5 micrometers.

* * * * *